US009327898B2

(12) United States Patent
van Dijk et al.

(10) Patent No.: US 9,327,898 B2
(45) Date of Patent: May 3, 2016

(54) AEROSOL SPRAY PRODUCTION (71) Applicant: Conopco, Inc., Englewood Cliffs, NJ (US)

(72) Inventors: Nicholas Joseph van Dijk, Wirral (GB); Lynda Grainger, Broughton (GB); Anthony Moretta, Elton (GB); Brian Patrick Newby, Wirral (GB); Simon Andrew Watson, Appleton (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/409,032

(22) PCT Filed: Jun. 20, 2013

(86) PCT No.: PCT/EP2013/062841
§ 371 (c)(1),
(2) Date: Dec. 18, 2014

(87) PCT Pub. No.: WO2014/001185
PCT Pub. Date: Jan. 3, 2014

(65) Prior Publication Data
US 2015/0175340 A1   Jun. 25, 2015

(30) Foreign Application Priority Data

Jun. 26, 2012  (EP) ..................................... 12173547
Jul. 27, 2012  (EP) ..................................... 12178307

(51) Int. Cl.
*A62C 31/02*   (2006.01)
*B65D 83/30*   (2006.01)
(Continued)

(52) U.S. Cl.
CPC .............. *B65D 83/30* (2013.01); *A61K 8/0241* (2013.01); *A61K 8/046* (2013.01); *A61Q 15/00* (2013.01);
(Continued)

(58) Field of Classification Search
CPC .................................. B05B 1/00; B65D 83/30
USPC ............. 239/337, 469, 491, 507, 533.13, 602
See application file for complete search history.

(56) References Cited

U.S. PATENT DOCUMENTS 3,982,605 A    9/1976  Sneckenberger
4,141,472 A *  2/1979  Spitzer .................. B65D 83/44
                                                       137/199

(Continued)

FOREIGN PATENT DOCUMENTS

AU   537811     7/1984
GB   1591312    6/1981
(Continued)

OTHER PUBLICATIONS

IPRP2 in PCTEP2013062841, dated Jul. 7, 2014; p. 1 to p. 11.
(Continued)

*Primary Examiner* — Len Tran
*Assistant Examiner* — Adam J Rogers
(74) *Attorney, Agent, or Firm* — Karen E. Klumas (57) ABSTRACT

A method and product for producing a soft sounding aerosol spray from a particulate suspension, said method and product involving a spray channel having an exit orifice of internal diameter of from 0.5 to 0.8 mm and a terminal section leading to the exit orifice of internal diameter from 0.5 to 0.8 mm for a length of 5 mm or greater, the terminal section of the spray channel including the exit orifice having a tubular internal surface free from obstacle.

11 Claims, 7 Drawing Sheets

(51) Int. Cl.
*A61K 8/04* (2006.01)
*B05B 1/00* (2006.01)
*B65D 83/20* (2006.01)
*B65D 83/14* (2006.01)
*A61Q 15/00* (2006.01)
*A61K 8/02* (2006.01)
*B65D 83/68* (2006.01)

(52) U.S. Cl.
CPC . *B05B 1/00* (2013.01); *B65D 83/20* (2013.01); *B65D 83/752* (2013.01); *B65D 83/753* (2013.01); *A61K 2800/412* (2013.01); *A61K 2800/87* (2013.01); *B65D 83/68* (2013.01)

(56) References Cited

U.S. PATENT DOCUMENTS

| | | | | | |
|---|---|---|---|---|---|
| 4,167,245 | A | * | 9/1979 | Kock | A45D 34/00 222/391 |
| 4,227,631 | A | * | 10/1980 | Schneider | 222/635 |
| 5,639,025 | A | * | 6/1997 | Bush | B05B 1/00 239/333 |
| 5,642,860 | A | * | 7/1997 | Bush | B05B 1/00 239/333 |
| 5,929,396 | A | | 7/1999 | Awad | |
| 6,659,313 | B1 | | 12/2003 | MacMurdo | |
| 2005/0098588 | A1 | * | 5/2005 | Dunne | B65D 83/62 222/402.24 |

FOREIGN PATENT DOCUMENTS

| | | |
|---|---|---|
| JP | 2010099600 | 5/2010 |
| WO | WO03051522 | 6/2003 |
| WO | WO2006133725 A1 | 12/2006 |

OTHER PUBLICATIONS

Search Report in EP12173547 dated Nov. 21, 2012; p. 12 to p. 13.
Search Report in PCTEP2013062841 dated Jul. 19, 2013; p. 14 to p. 16.
Written Opinion in EP12173547 dated Nov. 21, 2012; p. 17 to p. 19.
Written Opinion in PCTEP2013062841 dated Jul. 19, 2013; p. 20 to p. 24.

* cited by examiner

Fig. 8
0.7 mm Diameter

Fig. 9
0.8 mm Diameter

AEROSOL SPRAY PRODUCTION

The present invention concerns a method for producing aerosol sprays and products for so doing. In particular, the invention concerns a method for producing aerosol sprays from a particulate dispersion.

Numerous publications disclose the production of aerosol sprays. Very few of these publications suggest means by which the sound quality or acoustics of the aerosol spray production may be controlled.

U.S. Pat. No. 3,872,605 (Carborundum Company, 1976) discloses a silencer device for reducing the noise generated by compressed air or a compressed air-particulate mixture. The silencer has a bore of substantially constant diameter which is, within limits, larger than the nozzle bore for which the silencer is designed. The smallest diameter of nozzle bore disclosed is ⅜ inch, approximately equal to 9.5 mm.

U.S. Pat. No. 5,929,396 (Ewad, 1999) discloses a noise reducing diffuser consisting of an elongated enclosure with openings at each end that is attached to the output of a gas nozzle. Whilst not concerned with aerosol sprays per se, the gas flow modulation described involves a diffuser of diameter 125% to 175% wider than the nozzle with which it is associated and of length only about 1 inch (25.4 mm) longer than said nozzle. Nozzles of diameter 0.032 inch (0.81 mm) are disclosed.

JP 2010-99600 (Oriental Aerosol Industrial) discloses an aerosol product which suppresses the jetting sound to a low level, the method involving a foamed porous body in the spray path.

It is an object of the present invention to provide a means for producing aerosol sprays, in particular for application to the surface of the human body, that are perceived as sounding "soft" as they are produced. The aerosol sprays concerned are derived from particulates of mean particle size of from 5 to 100 microns dispersed in a liquefied organic propellant. It is a further object of the present invention to provide a means for producing aerosol sprays that are perceived as both sounding and feeling soft.

It is a further object of the present invention to avoid spray channel blockage during the production of such aerosol sprays.

In producing an aerosol spray that is perceived as sounding "soft", more factors are involved than merely its volume. We have found that whilst volume is a factor in consumers' perception of what sounds soft, lower volume typically equating with a softer sounding spray, other factors are also involved, notably the degree of modulation in the sound profile of the spray, something sometimes referred to by consumers as "splutter" or "harshness". Modulation of the sound profile in the region between 1000 and 5000 Hz has been found to be of particular importance. It is with maximising the overall perception of "soft sounding" with which the present invention is concerned.

The present invention is of particular value in applying cosmetic compositions to the surface of the human body. This is especially the case when the cosmetic composition is one that delivers "care" benefits, such as skin care benefits, like emolliency, for example. With cosmetic compositions that deliver care benefit, the soft sounding spray generated by the present invention can reinforce the consumer's perception of the product as being gentle and caring, augmenting the overall consumer experience.

The method of spray production disclosed herein typically involves a spray channel being attached to the valve stem of a pressurised vessel containing the composition to be sprayed. When the composition to be sprayed comprises particulate matter, the problem of valve blockage can arise, as well as possible blockage of the spray channel leading from the valve. Avoidance of these problems can make it even more difficult for a soft sounding spray to be produced.

In a first aspect of the present invention, there is provided a method for producing an aerosol spray from a composition comprising particulates of mean particle size of from 5 to 100 microns dispersed in a liquefied organic propellant, said method comprising the release of said composition from a pressurised vessel through a valve and an associated spray channel, characterised in that said spray channel has an exit orifice of internal diameter of from 0.5 to 0.8 mm and a terminal section leading to the exit orifice of internal diameter from 0.5 to 0.8 mm for a length of 5 mm or greater, the terminal section of the spray channel including the exit orifice having a tubular internal surface free from obstacle.

In a second aspect of the present invention, there is provided a product comprising particulates of mean particle size of from 5 to 100 microns dispersed in a liquefied organic propellant and means for producing an aerosol from said dispersion, said means comprising a spray channel having an exit orifice of internal diameter of from 0.5 to 0.8 mm and a terminal section of spray channel leading to the exit orifice having an internal diameter of from 0.5 to 0.8 mm for a length of 5 mm or greater, the terminal section of the spray channel including the exit orifice and having a tubular internal surface free from obstacle.

In a third aspect of the present invention, there is provided a method of producing an aerosol spray comprising the use of a product according to the first aspect of the invention.

In a fourth aspect of the present invention, there is provided a method for producing a soft sounding aerosol spray comprising the use of a product according to the second aspect of the invention.

For the aspects of the present invention that do not directly require a pressurised vessel capped by a valve, it should be understood that the present invention is designed for use in association with such a vessel.

Herein, the terms "aerosol" and "aerosol spray" may be used interchangeably and have the same meaning.

Herein, the "exit orifice" of the spray chamber is at the external end the terminal section of the spray chamber and is a part thereof.

Herein, the term "mean particle size" should be understood to refer to volume average particle size, D50. Particle size analysis may be by laser light scattering techniques, for example using a Malvern Mastersizer available from Malvern Instruments Ltd.

The present invention involves a particulate dispersion being sprayed from a spray channel having a terminal section of tightly defined parameters. The dispersed particulates have a mean particle size of from 5 to 100 microns, typically from 15 to 40 microns, and more typically from 20 to 30 microns.

Herein, mean particle sizes are volume mean particle sizes, measured as the D[4,3] or De Broncker mean diameter using light scattering techniques, optionally with laser light scattering equipment such as the Malvern Mastersizer.

In a preferred embodiment, the particulates are of an antiperspirant active intended for application to the surface of the human body. When this is the case, the size of the particulates can be of particular significance. Large antiperspirant particles can lead to blockage of the valve and/or the associated spray channel. It is preferred that at least 99% by weight of particles have a diameter below 100 microns and it is particularly preferred that at least 95% by weight of the particles have a diameter below 75 microns.

The particulates are typically present in the total composition at a level of from 1 to 20% and more typically at from 2% to 10% by weight.

The particulates are dispersed in a liquefied organic propellant, this mixture forming at least a part of a composition from which the aerosol spray is to be produced. The liquefied organic propellant may be selected from amongst those known in the art for such purpose. Examples of suitable propellants include trichlorofluoromethane, trichlorotrifluoroethane, difluoroethane, propane, butane or isobutane or combinations thereof. The amount used is typically from 5 to 95% and preferably from 30 to 90% by weight of the total composition.

The composition from which the aerosol spray is produced may comprise other components in addition to the particulates and liquefied propellant. A particularly preferred additional component is a carrier fluid that is liquid at ambient temperature (20° C.) and pressure (1 atmosphere). Typically, the carrier fluid is comprised of one or more water-immiscible oils. Suitable oils include silicone oils, ester and ether oils, fatty alcohols, and hydrocarbon oils.

Preferred carrier fluid oils for inclusion in the composition are emollient oils. Oils that help mask the particulate solid delivered from the aerosol spray may also be advantageously included.

Volatile silicone oils (having a vapour pressure of from 10 Pa to 2 kPa at 25° C.) are a preferred class of oil employed in a carrier fluid. They can be linear or cyclic and usually containing from 4 to 6 silicon atoms. Particularly preferred are dimethicones and cyclomethicones, such as cyclopentadimethylsiloxane (D5).

Suitable ester and ether oils include aliphatic esters selected from isopropyl myristate, lauryl myristate, isopropyl palmitate, diisopropyl sebacate, diisopropyl adipate, and glyceride oils (in particular triglyceride oils, such as sunflower seed oil). Suitable aromatic esters may also be incorporated such as $C_8$ to $C_{18}$ alkyl benzoates, including in particular $C_{12}$ to $C_{15}$ alkyl benzoates, e.g., those available under the trademark Finsolv.

Suitable hydrocarbon oils include liquid aliphatic hydrocarbons such as mineral oils or hydrogenated polyisobutene. Further examples are polydecene and paraffins and isoparaffins of at least 10 carbon atoms.

When employed, the carrier fluid is typically present at a level of from 1 to 30%, in particular from 2 to 20%, and especially from 5 to 10% by weight of the total composition.

Compositions used with the present invention may also comprise fragrance oil. When present, the amount of fragrance oil is normally from 0.01 to 3% by weight of the total composition.

Other components typical of those used in cosmetic aerosol compositions may also be employed, including suspending agents, such hydrophobically modified clays such as bentonite or hectorite.

Other minor ingredients which may be employed include anti-microbial agents, structurants (such as clays and silicas), polar additives (such as propylene carbonate), preservatives, antioxidants, and humectants (such as polyols, including glycerol).

In preferred embodiments, the particulates employed in the present invention comprise an antiperspirant active. Typically such an antiperspirant active is an aluminium salt, more particularly, a basic aluminum salt such as aluminum chlorohydrate.

The terminal section of the spray channel used in the present invention is a key component. Surprisingly, the present inventors have found that the sound quality of the spray produced is most sensitive to this particular component of the spray channel. In order to produce a soft sounding spray, it is essential that the terminal section of the spray channel has an internal diameter of from 0.5 to 0.8 mm and it is preferred this is from 0.6 to 0.8 mm, in particular greater than 0.6 mm to 0.8 mm. It is also essential that the terminal section has a tubular internal surface that is free from obstacle and that it extends for a length of 5 mm or more back from the exit orifice which is at its terminal end.

Being "free from obstacle" means that the terminal section of the spray channel is free from any obstacle that would impede the flow of a fluid passing through it. Typical of such an obstacle would be a projection into the spray channel from its internal surface. In most embodiments, the internal surface of the terminal section of the spray channel is a smooth tube, of uniform cross-section or tapered. Typically, there is nothing in the terminal section of the spray chamber to significantly increase the turbulence of flow of a fluid passing through it.

Fluid flow through the terminal section of the spray channel may be studied using CFD (Computer Fluid Dynamics) techniques known in the art.

The "length" of the terminal section of spray chamber refers to the distance from the exit orifice for which the spray chamber meets the other requirements of this feature, i.e. has an internal diameter of from 0.5 mm (preferably 0.6 mm) to 0.8 mm and a tubular internal surface that is free from obstacle.

Preferably, the length of spray channel is from 5 mm to 15 mm and more preferably from 5 to 11 mm. Whilst there is no evidence to suggest that longer lengths have a detrimental effect upon the acoustics of the spray produced, they are harder to produce and can lead to increased blockage.

In all preferred embodiments, the tubular internal surface of the terminal section of the spray chamber has a circular cross-section along its entire length.

The terminal section of the spray channel may be of constant internal diameter or it may taper. When it tapers, it preferably increases in internal diameter towards the exit orifice. Preferably, any taper is such that the minimum internal diameter of the terminal section of the spray channel is up to 0.2 mm less than internal diameter of the exit orifice. It may be noted that when the internal diameter is from 0.6 mm to 0.8 mm, the taper could be no greater than 0.2 mm in any event. When tapered spray section terminal sections are involved, it is particularly preferred that that said sections are of circular cross-section.

Tapering spray channel terminal sections that increases in internal diameter towards the exit orifice have been found to be particularly beneficial in delivering the dual benefits of an aerosol spray that is perceived as both sounding soft and feeling soft. Such dual benefits can augment one another and synergise the user's perception of "soft and caring" from the product being sprayed.

The terminal section of the spray channel has a ratio of length to internal diameter that is preferably from 6:1 to 20:1 and more preferably from 7.5:1 to 15:1.

The preferred spray rate on using product and/or method of the present invention is from (0.65 to 1.1 g/s), although it must be noted that this value can be significantly altered by factors other than those specified in the features claimed.

The preferred sound intensity on using product and/or method of the present invention is from 70 dB to 82 dB, as measured by the method described in the Examples that follow, although it must be noted that this value can be significantly altered by factors other than those specified in the features claimed.

EXAMPLES

The following examples make reference to the following drawings, images and sound profiles.

In a first series of experiments, a large number of spray channel components were evaluated. FIGS. 1 to 4 illustrate the arrangement used. The components were housed in the grooves (7) of an aluminium "mule" (1), comprised of an upper (4) and lower half (5), which was in turn connected to a commercially available antiperspirant aerosol product (6) (a 175 ml Dove™ antiperspirant aerosol, sprayed down to a 75% fill level before use). The mule sat on the valve stem of the aerosol container (6) such that downward pressure on the mule (1) caused the opening of the valve and allowed release of the pressurised contents therein. The valve stem fed into the mule (1) through a passageway (8) in a lower side of a chamber (9) of the mule (1) in fluid connection with a first segment of the spray channel (2A or 2B) (see FIGS. 1A and 1B). The first segment of the spray channel (2A or 2B) was held in close proximity to and in fluid communication with the second (terminal) segment (3) of the spray channel. All of the components of the mule (1) were made of aluminium. In use, upper (4) and lower (5) halves of the mule (1) were held together by four tightening screws (9A) fitting through threaded holes (9B) to give an airtight assembly for the mule. It will be noted that the exit orifice (10) for the mule was significantly wider than the internal diameters of the exit orifices of the spray chambers (not shown) that sprayed through it (vide infra).

Two mules (1) were used: one having a central groove (7A) (not illustrated) dimensioned to accept a 3 mm first segment (2A) of the spray channel and another having a groove (7B) dimensioned to accept a 5 mm first segment (2B) of the spray channel. Both mules (1) had a groove (7C) dimensioned to accept a 5 mm second (terminal) segment (3) of the spray channel.

The sound and spray rate produced by the various combinations of components were evaluated by the methods described below.

Spray rate is a measure of the amount of product discharged from the can expressed as grams per second (g/s). The aerosol can is weighed before and after a 5 second spray. Data reported are the average of three measurements.

Sound recordings were made using a Radio Shack Level Meter (model 33-20550 with the gain on the microphone set to 80 dB. The sound profile was saved as a WAV file using Audacity™ software. The start and end (0.25 sec.) of sound files were deleted and the power spectral density of the remainder was calculated using Welch's method on MATLAB. Sound intensity in dB was calculated as $10 \cdot \log_{10}$ [root mean square(wave intensity)].

Figure 1A:
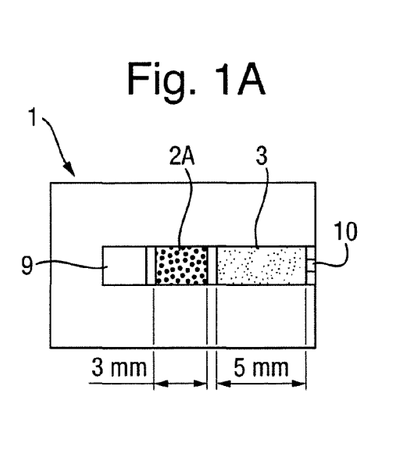
FIG. 1A is a plan view of a "mule" (1) holding a 3 mm first spray channel segment (2A) and a 5 mm second spray channel segment (3).
Figure 1B:
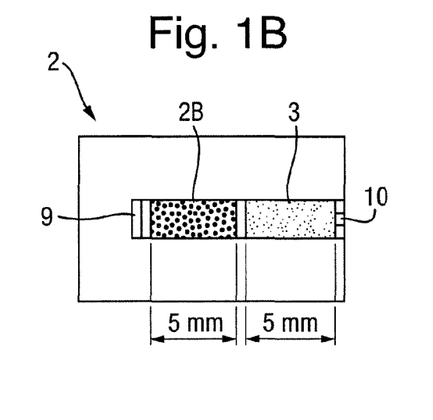
FIG. 1B is a plan view of a mule (1) holding a 5 mm first spray channel segment (2B) and a 5 mm second spray channel segment (3).
Figure 2:
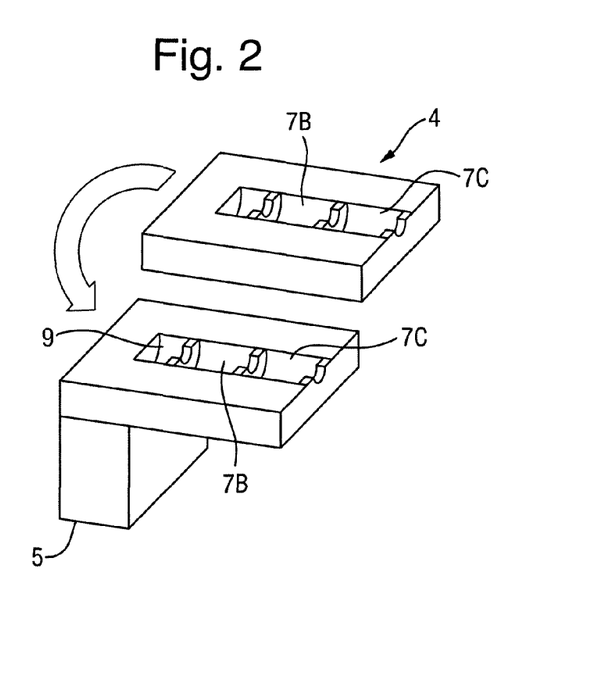
FIG. 2 is a rough sketch of an upper half (4) and a lower half (5) of a mule (1).
Figure 3A:
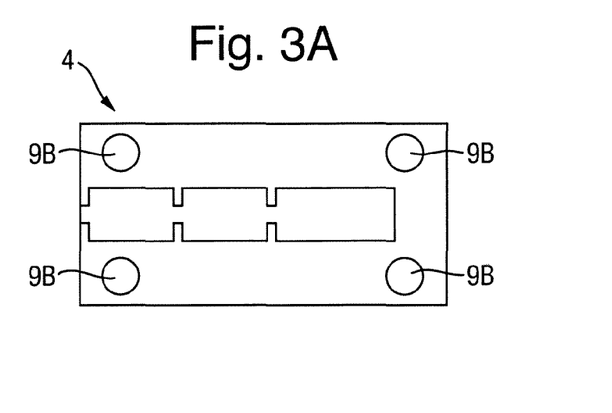
FIGS. 3A, 3B, and 3C are dimensioned representations of a mule, 3A being a view of an upper half (4) from below, 3B being a view of a lower half (5) from above, and 3C being a side view from of the same lower half (5).
Figure 3B:
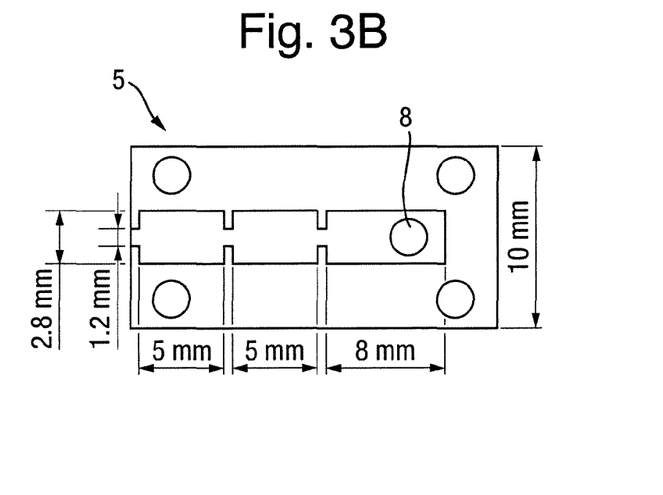
Figure 3C:
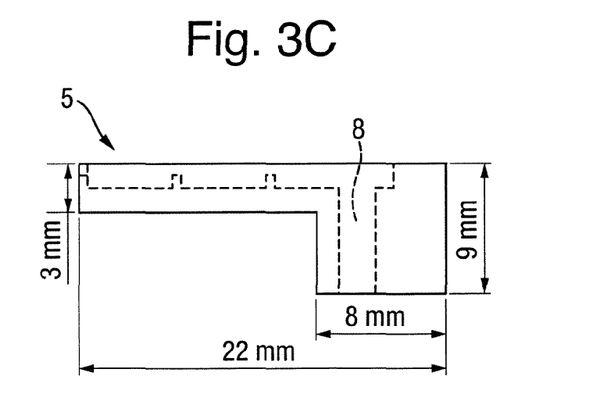
Figure 4:
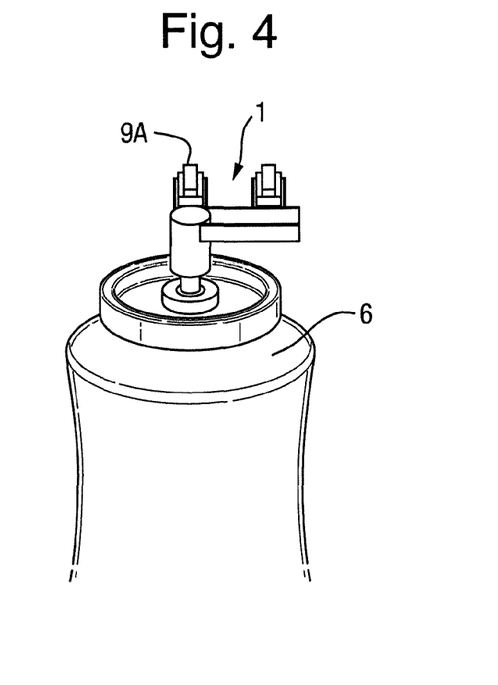
FIG. 4 is an image of a mule affixed to the valve stem of a commercially available antiperspirant aerosol container (6).
Figure 5:
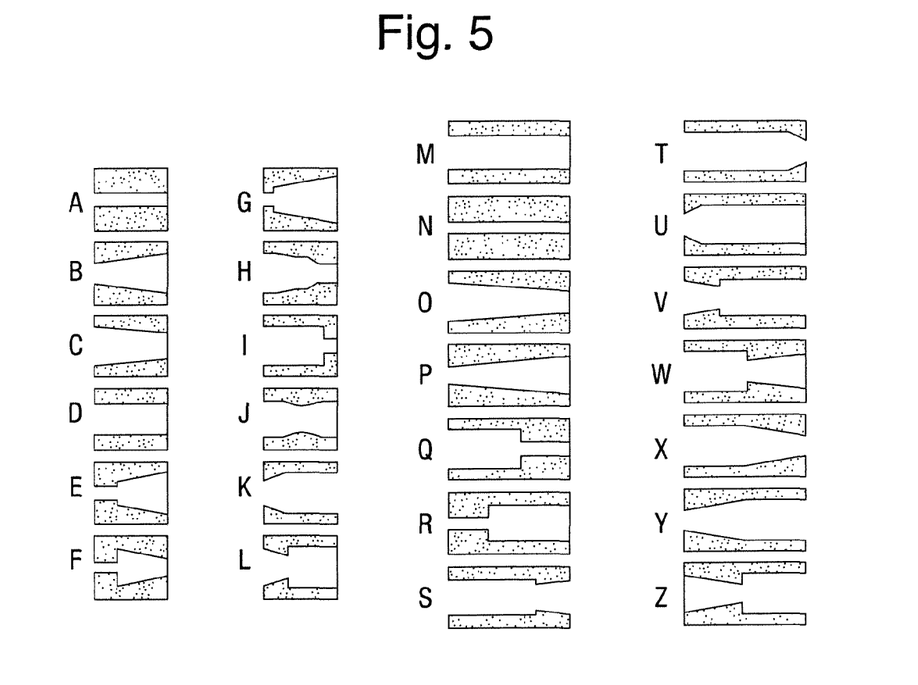
FIG. 5 illustrates the cross-sections of the first spray channel segment used to generate the data given in Table 1.
Figure 6:
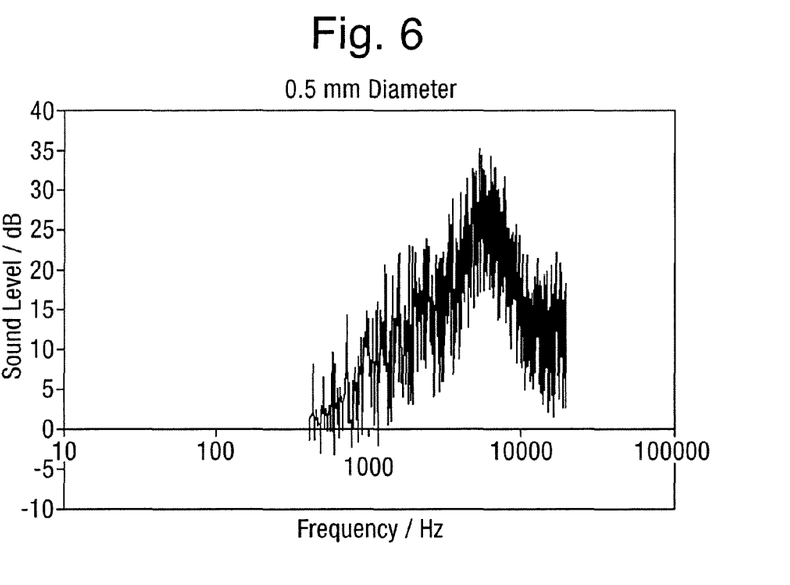
FIG. 6 is the sound profile produced from use of Example 36.
Figure 7:
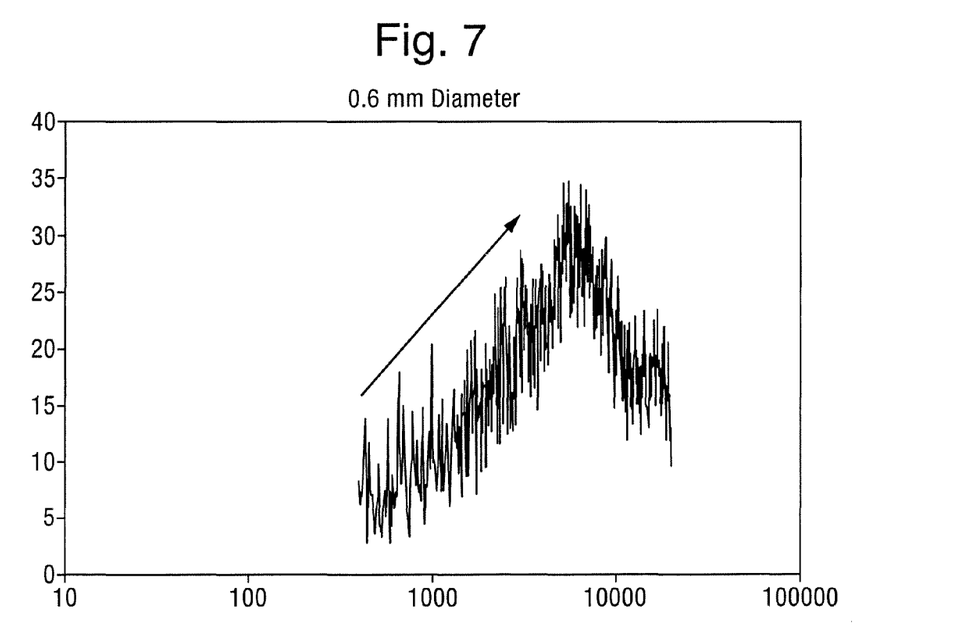
FIG. 7 is the sound profile produced from use of Example 37.
Figure 8:
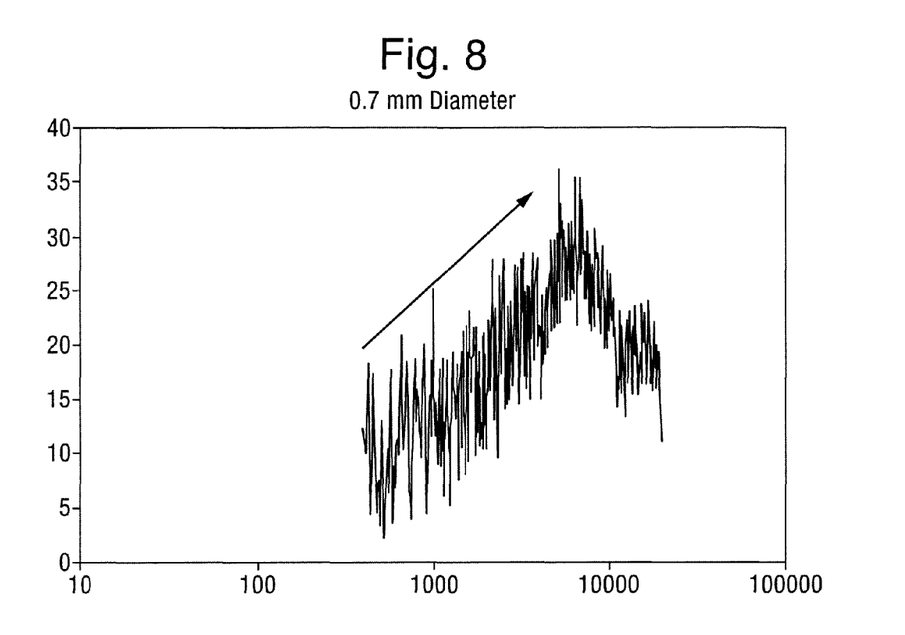
FIG. 8 is the sound profile produced from use of Example 38.
Figure 9:
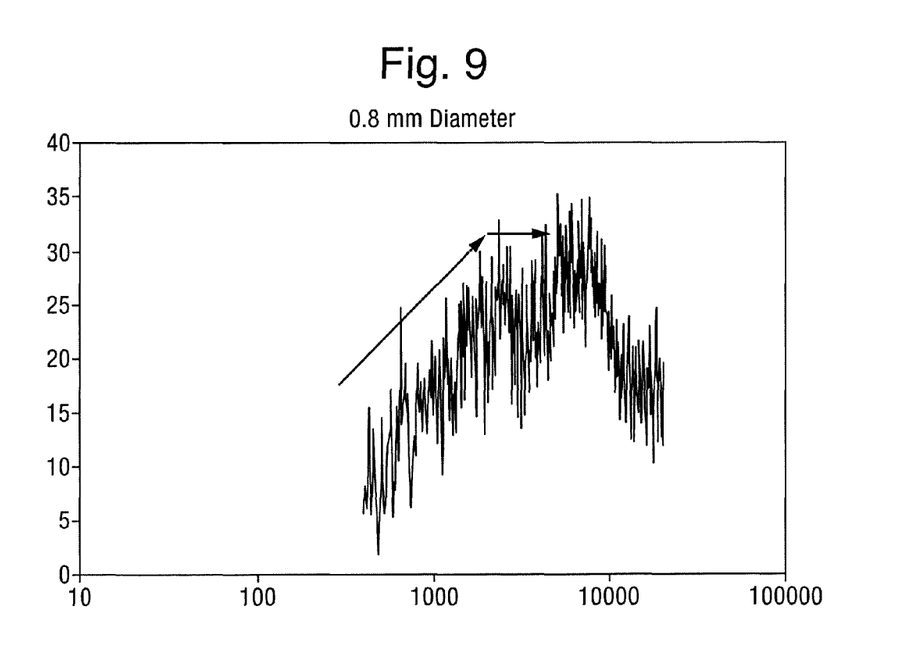
FIG. 9 is the sound profile produced from use of Example 39.
Figure 10:
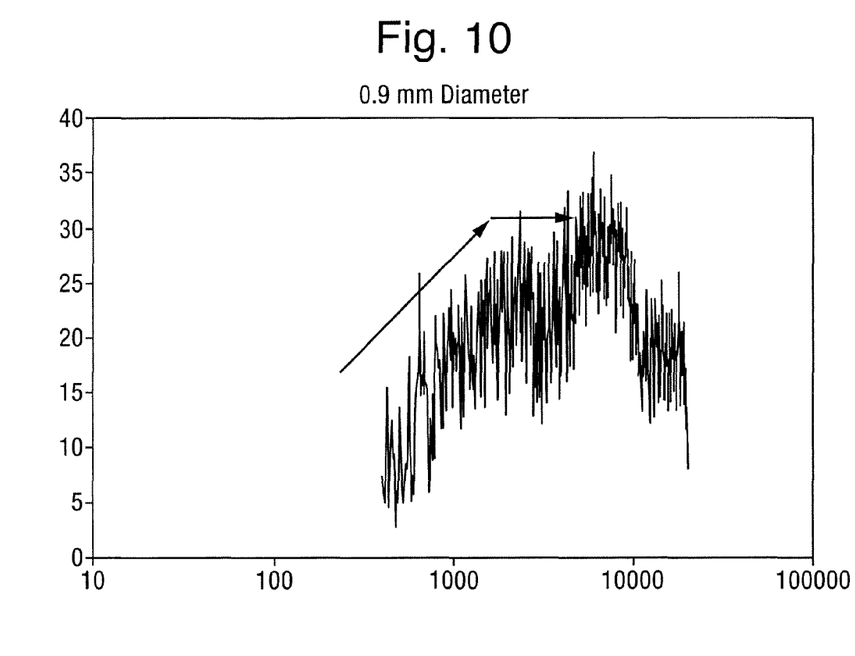
FIG. 10 is the sound profile produced from use of Comparative Example B.
Figure 11:
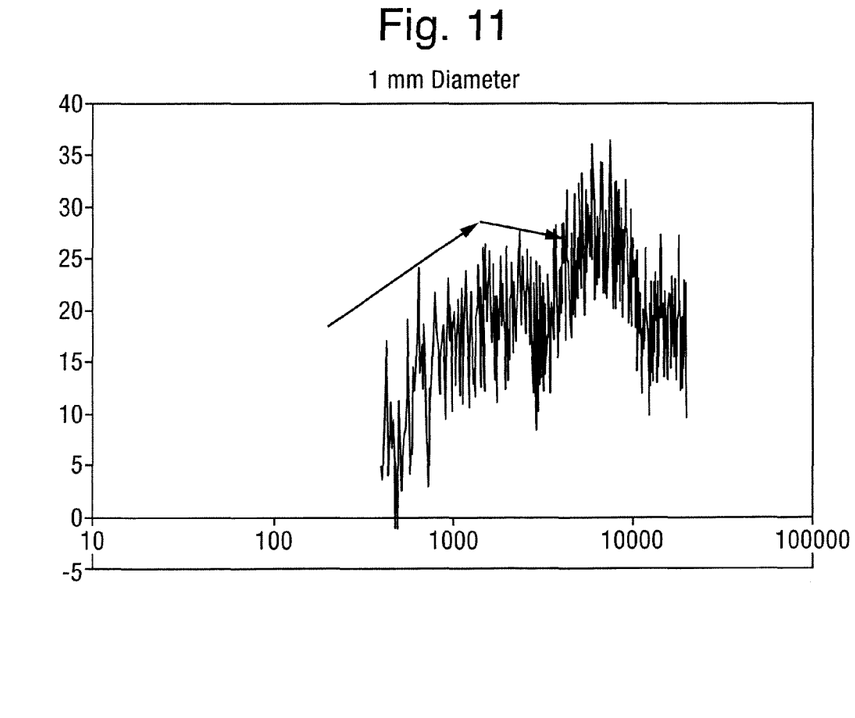
FIG. 11 is the sound profile produced from use of Comparative Example B.

The results in Table 1 show the effect of varying the first segment of the spray channel, keeping the second segment constant. The first segments, labelled A to Z were of length 3 mm (A to L) or 5 mm (M to Z) and are illustrated in FIG. 5. They were placed in the mule with the left hand side as illustrated closest to the passageway (8) from the valve stem. The second (terminal) segment of the spray channel was of length 5 mm and uniform internal diameter of 0.5 mm.

The results in Table 1 illustrate the fact that the large variations in the nature of the first segment have remarkably little effect on the spray rate and sound intensity. This illustrates the over-riding influence of the terminal segment of the spray channel, which for these experiments was kept constant. The range of spray rates found in this study was from 0.6 to 0.9 g/s and the range of sound intensities was from 83 to 87 dB.

TABLE 1

| Example | First segment used | Spray rate (g/s) | Sound Intensity (dB) |
|---|---|---|---|
| 1 | A | 0.68 | 85.6 |
| 2 | B | 0.70 | 86.4 |
| 3 | C | 0.75 | 85.3 |
| 4 | D | 0.64 | 85.1 |
| 5 | E | 0.66 | 84.6 |
| 6 | F | 0.64 | 83.7 |
| 7 | G | 0.64 | 84.1 |
| 8 | H | 0.78 | 84.7 |
| 9 | I | 0.62 | 83.1 |
| 10 | J | 0.60 | 82.8 |
| 11 | K | 0.67 | 84.7 |
| 12 | L | 0.69 | 85.1 |
| 13 | M | 0.90 | 86.1 |
| 14 | N | 0.69 | 84.8 |
| 15 | O | 0.76 | 85.4 |
| 16 | P | 0.73 | 84.9 |
| 17 | Q | 0.78 | 84.5 |
| 18 | R | 0.78 | 85.2 |
| 19 | S | 0.71 | 84.9 |
| 20 | T | 0.71 | 84.8 |
| 21 | U | 0.75 | 85.4 |
| 22 | V | 0.74 | 86.4 |
| 23 | W | 0.89 | 86.5 |
| 24 | X | 0.76 | 85.3 |
| 25 | Y | 0.75 | 87.1 |
| 26 | Z | 0.79 | 86.3 |

The results given in Table 2 were generated using a first segment of internal diameter (I.D.) 1.2 mm and length of 3 mm or 5 mm, coupled with second (terminal) segments each having a length of 5 mm. The tapered segments expanded outward in a linear fashion from the lower indicated diameter to the higher indicated diameter. The "straight" segments were of uniform diameter.

The aerosol product used comprised particulates having a mean particle size (D[4,3]) of 25 micron, +/−5 micron, dispersed in a liquefied organic propellant.

TABLE 2

| Example | First segment length (mm) | Second (terminal) 5 mm segment Nature | Second (terminal) 5 mm segment I.D. (mm) | Spray rate (g/s) | Sound Intensity (dB) |
|---|---|---|---|---|---|
| 27 | 3 | Straight | 0.5 | 0.71 | 84 |
| 28 | | Straight | 0.7 | 0.90 | 81 |
| 29 | | Tapered | 0.5 to 0.7 | 0.68 | 80 |
| 30 | 5 | Straight | 0.5 | 0.71 | 81 |
| | | | | 0.71 | 78 |
| 31 | | Straight | 0.6 | 0.78 | 82 |
| 32 | | Straight | 0.7 | 0.93 | 83 |
| | | | | 0.86 | 82 |
| 33 | | Tapered | 0.5 to 0.7 | 0.72 | 79 |
| | | | | 0.72 | 79 |
| 34 | | Tapered | 0.6 to 0.7 | 0.79 | 79 |
| 35 | | Tapered | 0.6 to 0.8 | 0.82 | 80 |
| A | | Tapered | 0.7 to 0.9 | 1.66 | 85 |

Looking at the results in Table 2, one can see a variation in spray rate of from 0.68 to 1.66 g/s and a variation in sound intensities of from 78 to 85 dB. This clearly illustrates the sensitivity of the spray rate and sound intensity to the nature of the terminal segment of the spray channel.

It may also be noted that Comparative Example A, having a terminal segment of internal diameter 0.9 mm at its outer edge, gave a spray rate of 1.66 g/s, well above the desired range (0.65 to 1.1 g/s).

When one compares the result for a given second segment in combination with the 3 mm first segment with that for the same second segment in combination with the 5 mm first segment (Example 27 vs. Example 30; Example 28 vs. Example 32; and Example 29 vs. Example 33), one can see that the results are remarkably similar. It would therefore appear that, across a range of second segments, the length of the first segment has little effect on the spray produced.

The results given in Table 3 were generated using a first segment of 5 mm length and a second segment of 5 mm length, the two segments each having the same internal diameter as indicated. In effect, this gave the spray channel a terminal segment of 10 mm length (ignoring the small gap between the segments) and internal diameters as indicated.

TABLE 3

| Example | Internal diameter (mm) | Spray rate (g/s) | Sound Intensity (dB) | Sound harshness | Sound profile Figure |
|---|---|---|---|---|---|
| 36 | 0.5 | 0.62 | 77 | Acceptable | 6 |
| 37 | 0.6 | 0.87 | 82 | Acceptable | 7 |
| 38 | 0.7 | 0.96 | 82 | Acceptable | 8 |
| 39 | 0.8 | 1.07 | 83 | Somewhat harsh | 9 |
| B | 0.9 | 1.25 | 83 | Unacceptably harsh | 10 |
| C | 1.0 | 1.37 | 83 | Unacceptably harsh | 11 |

From Table 3, it may be seen that the internal diameter has little effect on overall sound intensity, but does have a major effect on the "harshness" of the sound produced. FIGS. 6 to 11 show the sound profiles produced from Examples 36 to 39 and Comparative Examples B and C. It may be seen that the sound profiles produced by Examples 36 to 38 have a smooth increase in sound level across the frequency range from 1000 Hz to 5000 Hz, indicative of a soft sound, lacking any great harshness. The sound profile produced by Example 39, on the other hand, does not smoothly increase in sound level beyond about 2000 Hz, indicative of a somewhat harsh sound quality and the sound profiles produced by Comparative Examples B and C are even less smooth, indicative of a harsh sound quality.

It will also be noted from Table 2 that Comparative Examples B and C had a higher spray rate than desired (0.65 to 1.1 g/s) and that Example 36 had a slightly lower spray rate than desired.

Figure 12:
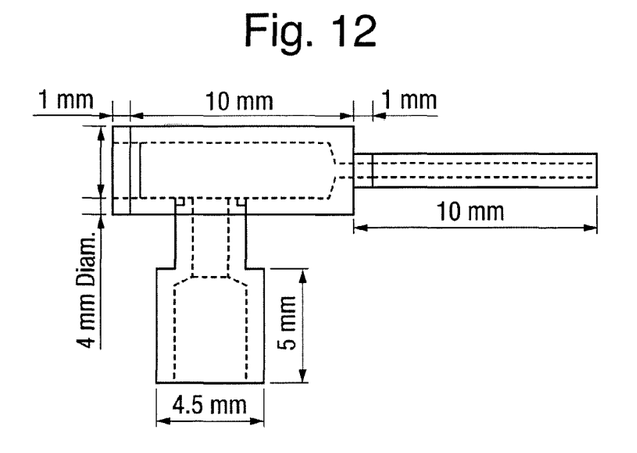
FIG. 12 is a representation of a plastic spray channel used in generating the data of Table 4.
Figure 13:
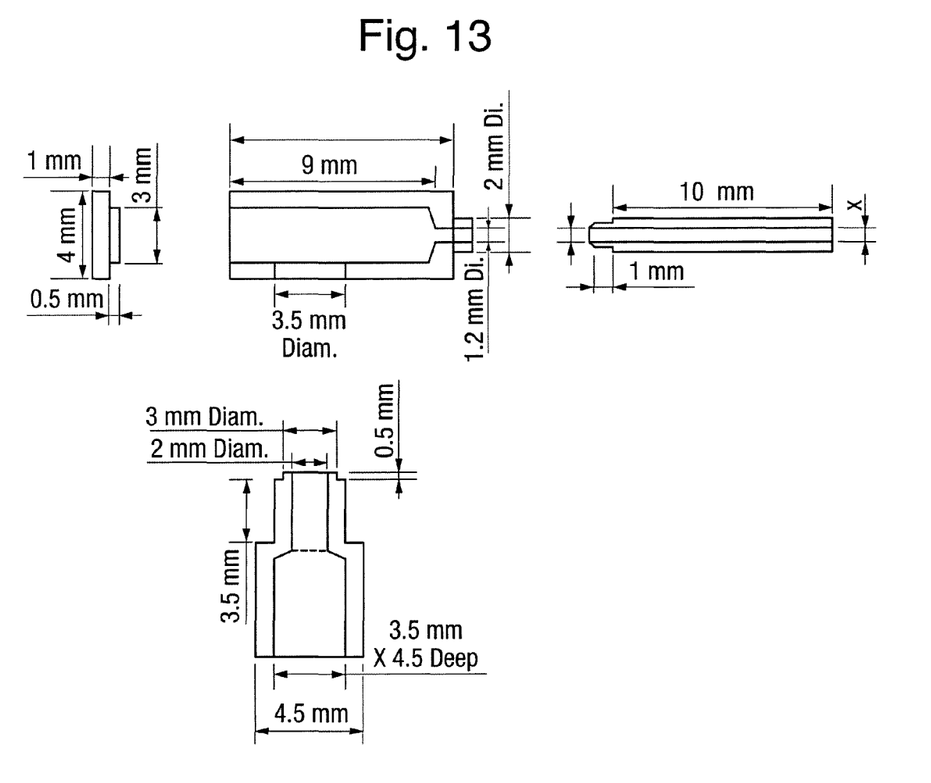
FIG. 13 is an exploded view of the same spray channel.

In a second series of experiments, spray channels as illustrated in FIGS. 12 and 13 were used. These spray channels were prepared from solid pre-moulded plastic (acetal) segments which were drilled to give the required internal profiles and glued together using a pressure adhesive. FIGS. 12 and 13 illustrate spray channels having an 11 mm terminal section; other lengths were also manufactured, as detailed below. The terminal section of the spray channels were of internal diameter "x", where x=0.5 or 0.6 mm. These terminal sections were affixed to other sections as illustrated in FIGS. 12 and 13. It will be noted that the section immediately preceding the terminal section had an internal diameter of 3 mm for most of its length, narrowing to 1.2 mm for a short distance just before the terminal section. It may also be noted that a 1 mm portion of the terminal section slots into the section immediately preceding it.

These spray channels were used in the same manner as the "mule" used in the earlier examples. Table 4 gives details of the effect of the length and internal diameter of the terminal section of the spray channel upon the spray rate and nature of the spray sound.

The "LMS" data given in Table 4 came from the use of a sound quality metric analysis developed by LMS™ Engineering Innovations. In essence, the system analyses the sound profile of a given spray and calculates a number that correlates with human perception of a given sound metric. The sound profiles generated in the present study had LMS metrics for "loudness", "softness" (low number=softer), and "splutter" calculated according to the following equations.

$$\text{LMS loudness} = \text{Zwicker loudness};$$

$$\text{LMS softness} = \text{roughness} + 0.018 \times \text{Zwicker loudness};$$

$$\text{LMS splutter} = \text{crest factor} + 0.018 \times \text{Zwicker loudness}.$$

The "softness" and "splutter" metrics involve a Zwicker loudness contribution because these metrics are significantly correlated with perceived loudness.

From Table 4, it can be seen that for each of the 0.5 mm internal diameter samples, the spray rate was somewhat less than desired, whereas the spray rate was within the desired range for each of the 0.6 mm internal diameter samples.

TABLE 4

| Length | Internal diameter (mm) | Spray rate (g/s) | Sound Intensity (dB) | LMS loudness | LMS softness | LMS splutter |
|---|---|---|---|---|---|---|
| 6 | 0.5 | 0.59 | 79.8 | — | — | — |
| 7 | | 0.60 | 79.6 | — | — | — |
| 8 | | 0.52* | 76.0* | 18.2 | 0.58 | 5.4 |
| 9 | | 0.60 | 81.7 | — | — | — |
| 10 | | 0.63 | 81.4 | 17.7 | 0.51 | 5.3 |
| 11 | | 0.60 | 80.6 | — | — | — |
| 6 | 0.6 | 0.66 | 78.6 | 17.7 | 0.47 | 5.0 |
| 7 | | 0.70 | 79.8 | 16.9 | 0.47 | 5.2 |
| 8 | | 0.68 | 79.1 | 16.2 | 0.44 | 5.0 |
| 9 | | 0.67 | 79.3 | — | — | — |

TABLE 4-continued

| Length | Internal diameter (mm) | Spray rate (g/s) | Sound Intensity (dB) | LMS loudness | LMS softness | LMS splutter |
|---|---|---|---|---|---|---|
| 10 | | 0.66 | 79.1 | — | — | — |
| 11 | | 0.65 | 77.6 | — | — | — |

*These data points believed to be somewhat inconsistent with others due to issues with manufacturing.

The data in Table 4 show little to discriminate between the samples on the basic sound intensity measurement as described earlier. On the other hand, the LMS data do seem to offer some discrimination. For a given internal diameter, it appears that "loudness" decreases with length and that "softness" increases with length (as indicated by lower numbers for this metric). The data also give support for the view that the 0.6 mm internal diameter samples are quieter, softer sounding, and have less splutter than the 0.5 mm samples.

The invention claimed is:

1. An apparatus comprising particulates of mean particle size of from 5 to 100 microns dispersed in a liquefied organic propellant and means for producing an aerosol from said dispersion, said means comprising a spray channel having an exit orifice of internal diameter of from 0.5 to 0.8 mm and a terminal section of spray channel leading to the exit orifice having an internal diameter of from 0.5 to 0.8 mm for a length of 5 mm or greater, the terminal section of the spray channel including the exit orifice and having a tubular internal surface free from obstacle, characterised in that the terminal section of the spray channel is tapered, wherein the spray channel is attached to a valve stem that is part of a valve of a pressurized vessel and wherein the spray channel is a separate component from the valve of the pressurized vessel, and wherein the apparatus is suitable for applying the aerosol to the surface of the human body at a spray rate of 0.65 to 1.1 g/s and a sound intensity of from 70 to 82 dB.

2. An apparatus according to claim 1, wherein the terminal section of the spray channel has an internal diameter of from 0.6 to 0.8 mm for a length of 5 mm or greater.

3. An apparatus according to claim 1, wherein the internal surface of the terminal section of the spray channel is a smooth tube.

4. An apparatus according to claim 1, wherein the terminal section of spray channel increases in internal diameter towards the exit orifice.

5. An apparatus according to claim 4, wherein the minimum internal diameter of the terminal section of the spray channel is up to 0.2 mm less than internal diameter of the exit orifice.

6. An apparatus according to claim 1, wherein the terminal section of spray channel has a length of from 5 mm to 11 mm.

7. An apparatus according to claim 1, wherein there is nothing in the terminal section of the spray chamber to significantly increase the turbulence of flow of a fluid passing through it.

8. An apparatus according to claim 1, wherein the particulates are of an antiperspirant active.

9. A method of producing an aerosol spray comprising the use of an apparatus according to claim 1.

10. A method of applying of a cosmetic composition to the surface of the human body comprising the use of an apparatus according to claim 1.

11. A method for producing an aerosol spray from a composition comprising particulates of mean particle size of from 5 to 100 microns dispersed in a liquefied organic propellant, said method comprising the release of said composition from a pressurised vessel through a valve and an associated spray channel, characterised in that said spray channel has an exit orifice of internal diameter of from 0.5 to 0.8 mm and a terminal section leading to the exit orifice of internal diameter from 0.5 to 0.8 mm for a length of 5 mm or greater, the terminal section of the spray channel including the exit orifice having a tubular internal surface free from obstacle, characterised in that the terminal section of the spray channel is tapered, wherein the valve includes a valve stem to which the spray channel attaches as a separate component from the valve, wherein the composition is released from the pressurized vessel at a spray rate of 0.65 to 1.1 g/s and at a sound intensity of from 70 to 82 dB.

* * * * *